United States Patent
Jaffe

(10) Patent No.: US 6,545,044 B2
(45) Date of Patent: Apr. 8, 2003

(54) COMPOSITIONS OF MATTER CONTAINING L-GLUTAMINE AND PYRIDOXAL-ALPHA-KETOGLUTARATE

(76) Inventor: Russell Jaffe, 10430 Hunter View, Vienna, VA (US) 22181

( * ) Notice: Subject to any disclaimer, the term of this patent is extended or adjusted under 35 U.S.C. 154(b) by 0 days.

(21) Appl. No.: 09/866,908

(22) Filed: May 30, 2001

(65) Prior Publication Data

US 2002/0188010 A1 Dec. 12, 2002

(51) Int. Cl.⁷ .................... A61K 31/215; A61K 31/195
(52) U.S. Cl. ...................................... 514/529; 514/563
(58) Field of Search ................................... 514/529, 563

(56) References Cited

U.S. PATENT DOCUMENTS 3,830,821 A * 8/1974 Roldan et al.

OTHER PUBLICATIONS

CA127:79108, Rhoads, et al, Am. J. Physiol., 1997, 272(5, Pt. 1), G943–G953, abstract.*

* cited by examiner

Primary Examiner—Rebecca Cook
(74) Attorney, Agent, or Firm—Morrison & Foerster LLP

(57) ABSTRACT

Compositions having synergistic effects which make it possible to obtain full beneficial effects of L-glutamine while avoiding the toxic effects that may accompany administration of L-glutamine. This benefit is attained by administration of L-glutamine in conjunction with pyridoxal-alpha-ketoglutarate (PAK). Compositions containing PAK:L-glutamine at a ratio (w/w) of from 1:1 to 1:10 are effective for providing beneficial effects of L-glutamine at nontoxic levels.

8 Claims, No Drawings

COMPOSITIONS OF MATTER CONTAINING L-GLUTAMINE AND PYRIDOXAL-ALPHA-KETOGLUTARATE

FIELD OF THE INVENTION

This invention relates to use of beneficial synergistic administration of L-glutamine in conjunction with pyridoxal-alpha-ketoglutarate (PAK) to stimulate repair of tissues dependent on high turnover of cells.

BACKGROUND OF THE INVENTION

The use of L-glutamine, a basic amino acid, to provide an energy source for cells having a rapid turnover, such as cells of the mucosa of the intestine, has been known. Patients in need of significant stimulation of growth and repair of intestinal mucosa include those who have undergone surgical resection of the intestine and those suffering from chronic diseases as enteropathy (atrophy of the intestine) and persistent inflammatory bowel syndrome (IBS). Furthermore, certain infectious diseases and treatment modalities such as administration of antibodies can cause severe damage to the gastrointestinal mucosa. However, large amounts of L-glutamine are needed to achieve clinical results. Concerns have been raised about the high dosages. The build-up of L-glutamine (derived from energy-producing deamination of L-glutamine), which can act as an exitoneurotoxin. The difficulty resulting from this effect has greatly decreased the use of L-glutamine to provide benefit to those needing tissue repair. Hence, there is need for treatment modalities that will provide the benefits of L-glutamine which are not accompanied by the metabolic imbalance and potential toxic side effects seen under prior regimens. While the compositions of the invention may be used for stimulation of growth and repair of other cells which usually undergo rapid replacement in the body, the cells of the intestinal mucosa offer a reliable model that is conventionally used to study stimulation of growth and repair of cells.

SUMMARY OF THE INVENTION

The instant invention provides compositions having synergistic effects which make it possible to obtain full beneficial effects available using L-glutamine whilst avoiding the toxic effects that may accompany administration of L-glutamine. This benefit is attained by administration of L-glutamine in conjunction with pyridoxal-alpha-ketoglutarate (PAK). Compositions containing PAK:L-glutamine at a ratio (w/w) of from 1:1 to 1:10 are effective for providing beneficial effects of L-glutamine at nontoxic levels.

DETAILED DESCRIPTION OF THE INVENTION

It is the purpose of this invention to provide L-glutamine with pyridoxal-alpha-ketoglutarate in appropriate dosage ratios that will stimulate significant growth and repair of cells which must undergo rapid replacement, including cells of the intestinal mucosa, without causing toxic effects associated with administration of large doses of L-glutamine. The L-glutamine and PAK (active agents) may be administered in one composition or separately. While the combination will usually be administered by mouth, it may be administered by other means such as by nasal gastric tube or through a line directly into the gastrointestinal tract, such as a line through the abdominal wall into the stomach. The PAK and L-glutamine in the suggested ratios may also be administered by retention enema or into openings formed when an ileostomy or colostomy is performed. For example, the combination therapy may be administered by instillation into the "resting" terminal portion of the colon to heal damaged mucosa when a later anastomosis of the portions of the colon is planned.

Compositions may be administered to other mucosal tissue by application to such tissue. For example, compositions may be administered to the respiratory tract as sprays.

Carriers used in delivery of the active agents will depend on the made of administration. When the active agents are administered orally, they may, for example, be administered in the form of capsules, caplets or tablets. Such compositions may contain, additionally, fillers such as starches and microcrystalline cellulose, sweeteners, flavorings and preservatives. When administered in liquid forms such as sprays or retention enemas they will typically be administered in water or buffered solutions such as saline, half-normal saline, lactated Ringer's solutions, etc.

The active agents may be given at a ratio of PAK:L-glutamine of about 1:1 to 1:10 w/w, though the more usual ratio will be from 1:2 to 1:5 w/w. The dosage of L-glutamine needed when administered with PAK is about 10% to 30% of that required to achieve similar stimulation of growth or repair when L-glutamine is given in the absence of PAK. The more preferred amount of L-glutamine administered is about 20% of that required to achieve similar stimulation of growth and repair when administered in absence of pyridoxal-alpha-ketoglutarate. Furthermore, the beneficial effects are usually noticeable in about ⅓ the amount of time required to provide noticeable improvement when L-glutamine alone is administered.

EXAMPLE 1

L-glutamine and pyridoxal-alpha-ketoglutarate (PAK) combinations

| Intestinal conditions | L-glutamine alone | | L-glutamine/PAK | |
|---|---|---|---|---|
| | dose | result* | dose** | Result# |
| IBS (6 yrs duration) | 3 gm | none | 3 gm/1 gm | 90% |
| | 15 gm | 25% | | |
| | 30 gm | 45% | | |
| | 60 gm | 85% | | |
| Ileitis (9 yrs duration) | 3 gm | 5% | 3 gm/1 gm | 85% |
| | 15 gm | 20% | 6 gm/2 gm | 98% |
| | 30 gm | 50% | | |
| | 60 gm | 90% | | |

* gives the percent of improvement upon administration of the L-glutamine alone, ** gm L-glutamine/gm PAK given together, and # is the percent of improvement when the L-glutamine/PAK combination is administered. (The L-glutamine and PAK were obtained from Sigma Chemical company.)

In view of the above, it is clear that synergistic effects are obtained when L-glutamine and PAK are administered simultaneously. Indeed, administration of the amount of glutamine required to obtain benefits of the combination therapy would not usually be considered acceptable under usual circumstances because of the toxic effects of the large amounts of L-glutamine that would have to be considered.

EXAMPLE 2

A composition for oral administration is prepared:

| | |
|---|---|
| L-glutamine | 3 gm |
| pyridoxal-alpha-ketoglutarate | 1 gm |
| Starch | 2 gm |

The composition is sufficient to fill 3 capsules or may be administered by mouth as a powder.

EXAMPLE 3

Composition for administration as a retention enema or for installation into a colostomy stoma:

| | |
|---|---|
| L-glutamine | 6 gram |
| pyridoxal-alpha-ketoglutarate | 2 gram |

Add lactated Ringer's solution to 100 ml.

EXAMPLE 4

Composition for administration as a spray or retention enema:

| | |
|---|---|
| L-glutamine | 3 gram |
| pyridoxal-alpha-ketoglutarate | 1 gram |

Add half normal saline to 100 ml.

While the compositions of the invention have been tested on patients suffering from disorders affecting the intestinal mucosa, the methods of the invention are appropriate for use in treating other diseases wherein stimulation of cell growth or repair of cells with natural rapid turn-over is desirable. Such diseases include, but are not limited to, leaky gut syndrome and other diseases of maldigestion, chronic fatigue syndrome, fibromyalgia, diabetes, thyroiditis and chronic viral diseases. The combination therapy described herein will, by enhancing the growth and the repair of intestinal cells, increase the ability of the intestinal wall to reject and neutralize parasites and inhibit overgrowth of fungal organisms.

I claim:

1. A composition of matter comprising, pyridoxal-alpha-ketoglutarate and L-glutamine in a ratio of pyridoxal-alpha-ketoglutarate to L-glutamine of 1:1 to 1:10 w/w.

2. The composition of claim 1 wherein the ratio of pyridoxal-alpha-ketoglutarate to L-glutamine of 1:2 to 1:5 w/w.

3. The composition of claim 1 wherein the ratio of pyridoxal-alpha-ketoglutarate to L-glutamine is about 1:3 w/w.

4. A method of stimulating cell growth or repairing cells with natural rapid turn-over comprising administration of L-glutamine in conjunction with pyridoxal-alpha-ketoglutarate wherein the amount of L-glutamine is 10 to 30% of the effective amount of L-glutamine administered alone to attain stimulation of cell growth and repair in intestinal mucosal cells.

5. The method of claim 4 wherein the amount of L-glutamine administered is about 20% of the effective amount of L-glutamine administered alone to attain stimulation of cell growth and repair in intestinal mucosal cells.

6. The method of claim 4 wherein the L-glutamine and pyridoxal-alpha-ketoglutarate are given in a composition comprising pyridoxal-alpha-ketoglutarate:L-glutamine ratio of from 1:1 to 1:10 w/w.

7. The method of claim 6 wherein the composition given comprises pyridoxal-alpha-ketoglutarate:L-glutamine ratio of from 1:2 to 1:5 w/w.

8. The method of claim 6 wherein the composition given comprises pyridoxal-alpha-ketoglutarate:L-glutamine ratio of about 1:3 w/w.

* * * * *

UNITED STATES PATENT AND TRADEMARK OFFICE
CERTIFICATE OF CORRECTION

PATENT NO.   : 6,545,044 B2
DATED         : April 8, 2003
INVENTOR(S) : Russell Jaffe It is certified that error appears in the above-identified patent and that said Letters Patent is hereby corrected as shown below:

Column 3,
Line 16, please change "installation" to -- instillation --.

Signed and Sealed this

First Day of July, 2003

JAMES E. ROGAN
*Director of the United States Patent and Trademark Office*